(12) United States Patent
Jongerius et al.

(10) Patent No.: US 10,365,197 B2
(45) Date of Patent: Jul. 30, 2019

(54) OPTICAL PARTICLE SENSOR AND SENSING METHOD

(71) Applicant: KONINKLIJKE PHILIPS N.V., Eindhoven (NL)

(72) Inventors: Michiel Johannes Jongerius, Eindhoven (NL); Gerben Kooijman, Eindhoven (NL); Koray Karakaya, Eindhoven (NL); Okke Ouweltjes, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 17 days.

(21) Appl. No.: 15/579,334

(22) PCT Filed: Jun. 6, 2016

(86) PCT No.: PCT/EP2016/062815
§ 371 (c)(1),
(2) Date: Dec. 4, 2017

(87) PCT Pub. No.: WO2016/198360
PCT Pub. Date: Dec. 15, 2016

(65) Prior Publication Data
US 2018/0217042 A1 Aug. 2, 2018

(30) Foreign Application Priority Data
Jun. 12, 2015 (EP) .................................. 15171916

(51) Int. Cl.
*G01N 15/00* (2006.01)
*G01N 15/02* (2006.01)
(Continued)

(52) U.S. Cl.
CPC .......... *G01N 15/0205* (2013.01); *G01N 15/06* (2013.01); *G01N 15/1459* (2013.01);
(Continued)

(58) Field of Classification Search
CPC ........ G01N 21/84; G01N 21/85; G01N 21/88; G01N 21/8806; G01N 21/8851;
(Continued)

(56) References Cited

U.S. PATENT DOCUMENTS 3,944,797 A    3/1976  Coulter
5,164,787 A *  11/1992 Igushi ................ G01N 15/0211
                                                         356/336
(Continued)

FOREIGN PATENT DOCUMENTS

WO     2008140816 A1    11/2008

OTHER PUBLICATIONS

D. M. Holstius et al. "Field calibrations of a low-cost aerosol sensor at a regulatory monitoring site in California" Atmospheric Measurement Techniques Discussions, vol. 7, No. I, Jan. 1, 2014 (Jan. 1, 2014), , pp. 605-632, XP055230788, DOI: 10.5194/amtd-7-605-2014 the whole document.

(Continued)

*Primary Examiner* — Gordon J Stock, Jr.

(57) ABSTRACT

An optical particle sensor has at least first and second threshold settings applied to an optical sensor or a sensor signal to obtain first and second optical sensor readings. The first and second optical sensor readings are processed to determine a parameter which is dependent on a type of pollution event. The parameter is used to determine from at least one of the first and second optical sensor readings a mass of all particles below a first particle size. In this way the mass of all particles below a desired size can be evaluated, even though the optical sensor may not be responsive to the smallest particles.

15 Claims, 13 Drawing Sheets

(51) Int. Cl.
*G01N 15/06* (2006.01)
*G01N 15/14* (2006.01)
*G01N 21/85* (2006.01)
*G01N 21/94* (2006.01)

(52) U.S. Cl.
CPC ............ *G01N 21/85* (2013.01); *G01N 21/94* (2013.01); *G01N 2015/025* (2013.01); *G01N 2015/03* (2013.01); *G01N 2015/1402* (2013.01); *G01N 2021/8578* (2013.01)

(58) Field of Classification Search
CPC ........... G01N 21/94; G01N 2021/8411; G01N 2021/8416; G01N 2021/8578; G01N 2021/8874; G01N 2021/8877; G01N 2021/8883; G01N 2021/8896; G01N 15/02; G01N 15/0205; G01N 15/03; G01N 15/10; G01N 15/14; G01N 15/1425; G01N 15/1429; G01N 15/1456; G01N 15/1459; G01N 2015/025; G01N 2015/035; G01N 2015/1043; G01N 2015/1081; G01N 2015/1087; G01N 2015/1093; G01N 2015/1402; G01N 2015/1461; G01N 2015/1477; G01N 2015/1486; G01N 2015/1488; G01N 2015/149; G01N 2015/1493; G01N 2015/1497

See application file for complete search history.

(56) References Cited

U.S. PATENT DOCUMENTS

| | | | | |
|---|---|---|---|---|
| 5,379,113 A * | 1/1995 | Niwa | ................. | G01N 15/0211 250/574 |
| 6,970,799 B2 * | 11/2005 | Kleefstra | ........... | G01N 15/0211 356/339 |
| 7,532,986 B2 * | 5/2009 | Carnegie | .................. | F24F 11/30 702/29 |
| 7,932,490 B2 * | 4/2011 | Wang | ................. | G01N 15/0205 250/287 |
| 8,154,723 B2 * | 4/2012 | Fu | ...................... | G01N 15/0205 356/335 |
| 8,269,639 B2 * | 9/2012 | Cole | ...................... | G01N 21/53 340/618 |
| 9,714,893 B2 * | 7/2017 | Driscoll | ................. | G01N 15/02 |
| 2009/0039249 A1 | 2/2009 | Wang | | |
| 2013/0229655 A1 * | 9/2013 | Kaye | .................. | G01N 15/0205 356/343 |
| 2015/0253165 A1 * | 9/2015 | Ajay | ......................... | G01F 1/66 73/28.01 |
| 2016/0116389 A1 * | 4/2016 | Cooper | .................. | G08B 17/10 356/340 |
| 2018/0231453 A1 * | 8/2018 | Kaye | .................. | G01N 15/1434 |

OTHER PUBLICATIONS

Tracy Allen: "De-construction of the Shinyei PPD42NS dust sensor", Fifth St, May 30, 2013 (May 30, 2013), XP055230847, Retrieved from the Internet: URL: http://taki ngspace.org/wp-content/uploads/ShinyeiPPD42NS Deconstruction TracyAllen.pdf—[retrieved on Nov. 24, 2015] the whole document.

Amanda L. Northcross et al: "A low-cost particle counter as a real time fine-particle mass monitor", Environ. Sci.: Processes Impacts, vol . 15, No. 2, Jan. 1, 2013 (Jan. 1, 2013) , pp. 433-439, XP055230319, ISSN: 2050-7887, DOI: 10.1039/C2EM30568B the whole document.

Philip J. Dacunto et al: "Determining PM 2.5 calibration curves for a low-cost particle monitor: common indoor residential aerosols", Environ. Sci.: Processes Impacts, vol . 17, No. 11, Oct. 15, 2015 (Oct. 15, 2015) , pp. 1959-1966, XP055230332, ISSN: 2050-7887, DOI: 10.1039/C5EM00365B, p. 1961, col. 2, paragraph 2—p. 1961, col. I, paragraph 3.

M.J. Jongerius, P.H. Bouma, D. Hayashi, G. Kooijman, O. Ouweltjes, R.F. Xue, and K. Karakaya, Evaluation of Shinyei PPD42 optical particle sensor, PR-TN2014/00237, Dec. 2014.

A.A. Roy, S.P. Baxla, T. Gupta, R. Bandyopadhyaya, and S.N. Tripathi, "Particles emitted from indoor combustion sources: size distribution measurement and chemical analysis", Inhalation Toxicology, Informa healthcare, iFirst, 1-12, 2009.

P.T. Chang, L.K. Peters, and Y. Ueno, "Particle Size Distribution of Mainstream Cigarette Smoke Undergoing Dilution", Aerosol Science and Technology, 4:2, 191-207, 2011.

H. Grimm and D.J. Eatough, Aerosol Measurement: The Use of Optical Light Scattering for the Determination of Particulate Size Distribution, and Particle Mass, including the Semivolatile Fraction, Journal of the Aire&Waste Management Association 59, 101-107, 2009.

* cited by examiner

OPTICAL PARTICLE SENSOR AND SENSING METHOD

This application is the U.S. National Phase application under 35 U.S.C. § 371 of International Application No. PCT/EP2016/062815, filed on Jun. 6, 2016, which claims the benefit of International Application No. 15171916.8 filed on Jun. 12, 2015. These applications are hereby incorporated by reference herein.

FIELD OF THE INVENTION

This invention relates to optical particle sensors and sensing methods.

BACKGROUND OF THE INVENTION

Particle sensors are for example used to measure the level of pollution in the air.

Low-cost systems are available based on the measurement of light scattered at the particles which pass along with an air flow through a detection volume in the sensor. This air flow is for example driven by a fan or a heater. Each particle is illuminated by a continuous light source and creates a light pulse with a duration determined by the passage time of the particle through the detection volume.

These pulses are amplified, filtered and counted in an electronics system. In addition to indicating the particle concentration level, such detectors can be used to drive the operation of an air purifier device.

Optical particle sensors typically give a particle count as the sensor output, and these numbers are then converted to mass concentration. However, this conversion usually deviates from reality, as different types of aerosol have different densities. This is a generic problem for all optical particle sensors.

Moreover, low cost optical sensors, are typically only sensitive for particles above a certain particle size (for example 700 nm). The so-called PM2.5 standard however needs to provide the mass of all particles below a size of 2.5 µm. In practice, particles below 700 nm do contribute to this mass, however they are not detected by the sensor. Therefore, the conversion of the number of particles counted by the detector to the total particle mass will be affected by the relative contribution of these small particles to the overall PM2.5 level. This contribution depends on the distribution of particle sizes in the air, which in turn depends on the type of pollution event.

SUMMARY OF THE INVENTION

There is therefore a need for a particle sensor which can use a low cost optical sensor but which can deliver accurate readings of the total particle mass below a particular particle size (e.g. 2.5 µm). The invention is defined by the independent claims. The dependent claims define advantageous embodiments.

According to examples in accordance with an aspect of the invention, there is provided an optical particle sensor, comprising:

an optical sensor which generates a sensor signal, wherein the sensor signal or an analysis of the sensor signal is controllable by applying a threshold setting, wherein the threshold setting dictates a particle size detection range captured by the sensor signal;

a controller adapted to:

apply at least first and second different threshold settings and receive corresponding first and second optical sensor readings;

process the first and second optical sensor readings to determine therefrom a parameter which is dependent on a type of pollution event; and use the parameter to determine from at least one of the first and second optical sensor readings a mass of all particles below a first particle size.

By obtaining optical sensor readings at least at two different threshold settings (either as separate sensed signals, or as readings derived by processing a single sensed signal), the sensor response to at least two different particle size ranges is obtained. The different optical sensor readings may then be processed to determine the nature of a pollution event as characterized by a particular parameter. For example, different pollution events have different characteristic particle size profiles, which result in different pairs of sensor signals. By way of example, the pollution events (various events that generates aerosols that are perceived as pollution) may be cooking with different types of ingredients at different temperatures, cigarette smoke, urban air pollution, burning candles, etc. The known characteristic particle size profiles for the different types of pollution event enable one or both of the optical sensor readings to be rescaled or otherwise processed so that an accurate mass conversion from optical sensor readings of all particles up to the first particle size may be obtained. This particle range includes particles below the lower detection limit of the optical sensor, for which the particle distribution cannot be measured. This may for example be calculated for a PM2.5 mass concentration value such as µg/m$^3$.

By taking account of the type of pollution event, a more accurate evaluation is possible of the contribution of the overall particle mass from small particles outside the measurement range of the optical sensor. An accurate mass concentration is thus determined based on a dynamic (i.e. multi-level over time) calibration/correction scheme used in converting from particle count information to mass distribution information.

There are at least two different types of pollution events, and hence at least two different parameters which can be obtained. There preferably are more different pollution events, for example 5 or more.

In one set of examples, the sensor has an input for receiving the threshold setting. The controller then adapts the signal applied to the threshold setting input in order to cause different sensor readings. In another set of examples, a wideband signal is received from the sensor and the application of thresholds is applied at the signal processing level rather than at the sensor level.

The invention thus aims to derive from the signals of the optical detector a parameter which is indicative of the shape of the particle size distribution. This parameter thus depends on the type of pollution event, namely it distinguishes between events with a dominant contribution of larger particles (such as from cooking or candle extinguishing events), and those with a dominant contribution of small particles (such as from outdoor pollution or cigarette smoke). That event characterization can be used to select a calibration factor for conversion to a full mass measurement, such as PM2.5.

The optical sensor is for example only sensitive to particles above a second particle size, below the first particle size. The sensor enables the gap in the sensitivity of the optical sensor for the smallest particles to be compensated.

The optical sensor may provide a measure of counts per unit time and optionally also a measure of low pulse occupancy percentage after digitization of the analog signal by a comparator. Low cost optical sensors are able to provide count and/or low pulse occupancy rates (LPO %). The invention can thus be implemented by a low cost optical sensor, for example based on the time during which a particle is seen by the optical sensor. Larger particles are seen by the sensor for longer hence give a larger signal both in amplitude (since the optical sensor integrates the detected signal) and also on the time axis. A threshold may be applied to the signal amplitude, and only particles above a certain size reach the threshold. A count of the pulses which reach the threshold enables a particle count to be measured. The LPO measure is based on the proportion of the time during which particles meeting the threshold are detected. Thus, a single low cost sensor can produce both LPO and particle count information.

The controller may be adapted to process the first and second optical sensor readings by:

combining a particle count per unit time for the first threshold setting and a low pulse occupancy rate for the second threshold setting; or combining a particle count per unit time for the first threshold setting and a particle count per unit time for the second threshold setting.

This provides two different ways to characterize the type of event. The combining for example comprises finding a ratio between the two values.

The first threshold setting may be for detecting a wider range of particle sizes than the second threshold setting. The first threshold setting for example is a lower threshold, so that the range of detected particles includes smaller particles than the range of detected particles for the second threshold setting.

The controller may be adapted to modify one of the first and second optical sensor readings based on the parameter to derive the sensed mass of all particles below the first particle size.

The modification may be based on a previously stored relationship between the parameter and a modification factor. The sensor preferably has a memory for storing such a relationship. The modification factor may be stored as a set of individual values each associated with a different event, such as a look up table. Alternatively, the mapping between the parameter and the modification factor may be a function. In the latter case, the type of pollution event does not need to be identified as such. Instead, the conversion from the parameter (which characterizes the event) to the modification factor takes account of the type of event without needing to identify the event specifically.

The sensor may comprise a display for displaying information conveying the mass of all particles below the first particle size, wherein the controller is adapted to generate a first mass signal and a second, moving average, mass signal, wherein the first mass signal is a real time sensor signal or a moving average signal averaged over a shorter duration than the second mass signal, and the processor is adapted to provide an output for display comprising one of the first and second mass signals. For slowly varying data, a moving point average signal provides a more accurate reading, whereas for rapidly varying data, a real time signal (i.e. with a shortest possible averaging window) or a signal with a shorter averaging window than the second signal, gives more information about the actual time at which an event takes place, such as a pollution spike.

The controller may be adapted to select one of the real time mass signal and the moving point average mass signal in dependence on the difference between them. This difference enables the sensor to determine if real time information is more important or if average information, which is more accurate but less time specific, is more important.

Examples in accordance with another aspect of the invention provide an optical particle sensing method, comprising:

operating an optical sensor to generate a sensor signal, and controlling the sensor or analyzing the generated sensor signal by applying at least first and second threshold settings to obtain first and second sensor readings, wherein the threshold setting dictates a particle size detection range captured by the sensor signal;

processing the first and second optical sensor readings to determine therefrom a parameter which depends on a type of pollution event; and using the parameter to determine from at least one of the first and second optical sensor readings a mass of all particles below a first particle size.

The method may comprise:

processing the first and second optical sensor readings by combining a particle count per unit time for the first threshold setting and a low pulse occupancy rate for the second threshold setting; or processing the first and second optical sensor readings by combining a particle count per unit time for the first threshold setting and a particle count per unit time for the second threshold setting.

The method may include displaying information conveying the mass of all particles below the first particle size, wherein the method further comprises generating a first mass signal and a second, moving average, mass signal, and displaying one of the first and second mass signals.

BRIEF DESCRIPTION OF THE DRAWINGS

Examples of the invention will now be described in detail with reference to the accompanying drawings, in which.

DETAILED DESCRIPTION OF EMBODIMENTS

The invention provides an optical particle sensor in which at least first and second threshold settings are applied to an optical sensor or sensor signal to obtain first and second optical sensor readings. They are processed to determine a parameter which is dependent on the type of pollution event. The parameter is used to determine from at least one of the first and second optical sensor readings a mass of all particles below a first particle size. In this way the mass of all particles below a desired size can be evaluated, even though the optical sensor may not be responsive to the smallest particles.

Figure 1:
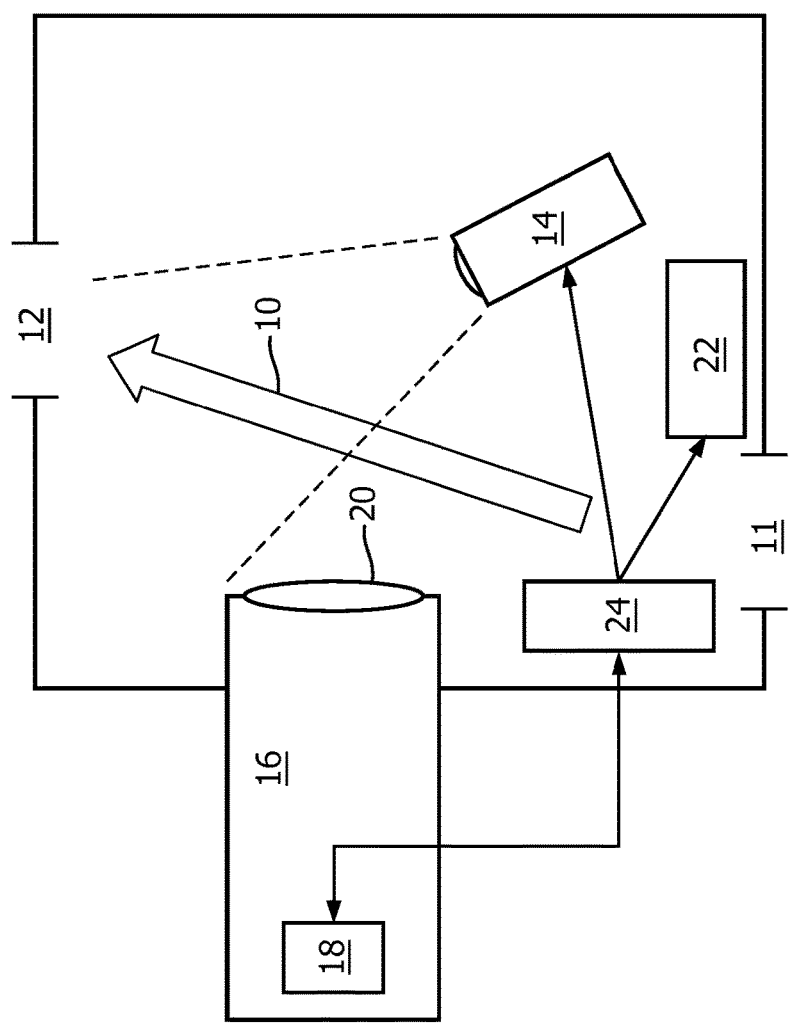
FIG. 1 shows an example of an optical sensor to which the invention may be applied.
Figures 2A, 2B:
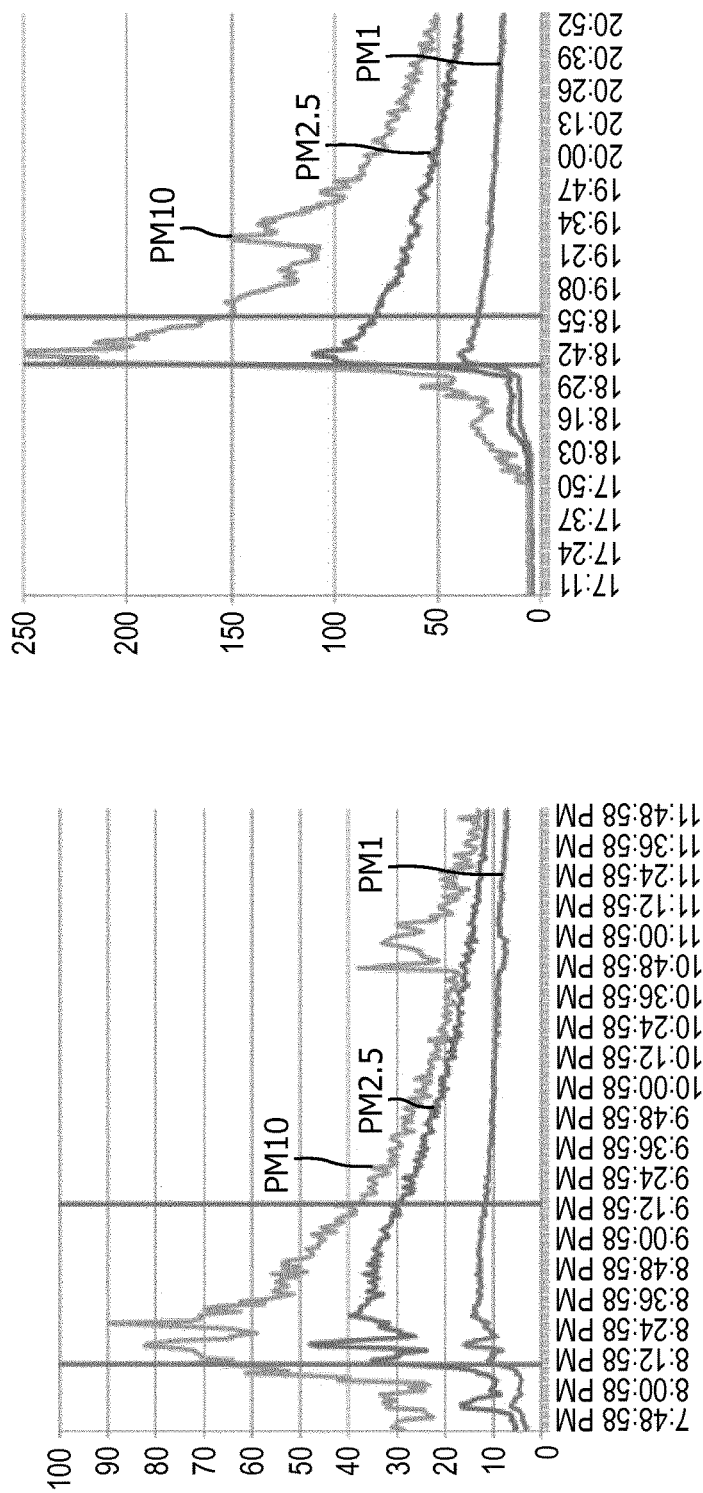
FIGS. 2a-2d show the result of monitoring various dinner events in a home.
Figure 2D:
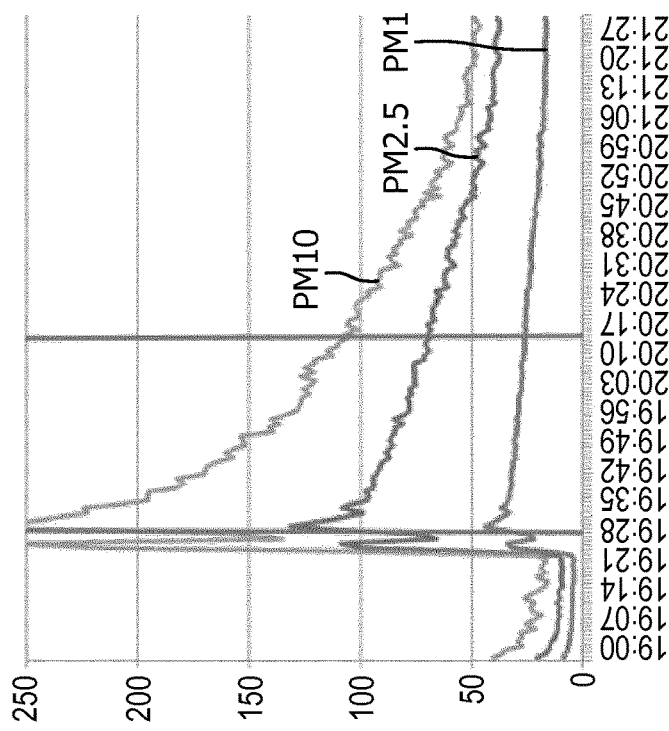
Figure 2C:
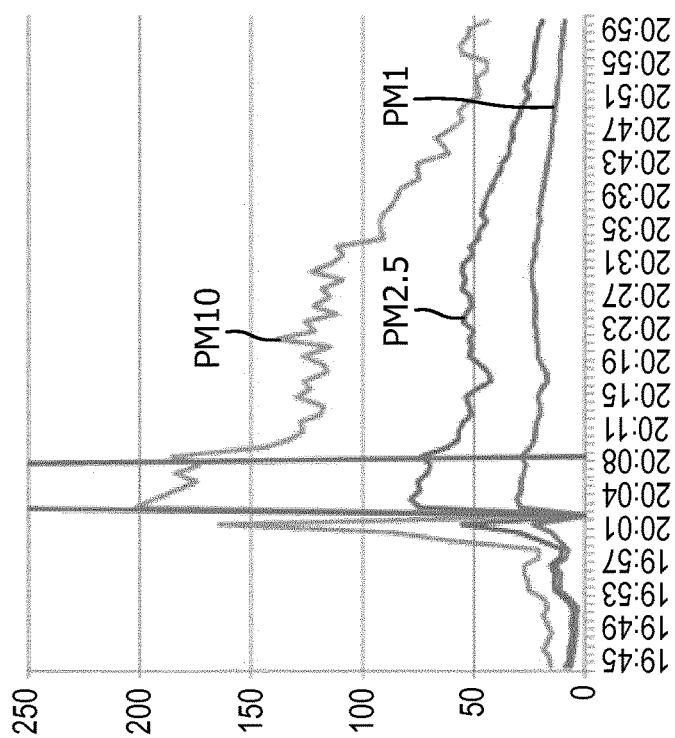

FIG. 1 shows an example of an optical sensor to which the invention may be applied. There is a gas flow 10 from an inlet 11 to an outlet 12 of the overall sensor device. An infrared LED 14 ($\lambda$=890 nm) is used to illuminate the gas flow to enable optical detection of entrained particles based on optical measurements of scattering. The LED is to one side of the detection volume and the sensing is carried out at the opposite side. An alternative design may make use of reflection of light.

The optical sensor 16 comprises a photodiode sensor 18 and a focusing lens 20 at which scattered light is collected.

A heater 22 is used for inducing convective flow through the sensor device. By the resulting buoyancy, the air flows towards the top of the detector, carrying the particles through the detection volume.

A controller 24 controls the processing of the sensor signals and operation of the heater and light source.

The detection volume is part of a housing which is placed on a printed circuit board with the electronics to convert the signal due to the particles into a count. The internal shape of the housing is such that leakage of LED light directly towards the photodiode sensor, which would give a background signal, is minimal. By electronically filtering out any remaining DC signal, the pulsed particle signal remains.

This signal is amplified and compared with a threshold voltage. Above a certain particle size, the peak height is sufficient to pass the threshold. The threshold thus implements a band pass filtering function. The pulse is counted and the pulse length is measured, resulting in a low-pulse occupancy time (LPO %).

Thus, there are two basic outputs. One is a simple particle count, which is a count of the number of detection peaks which exceed the threshold set. The other is the proportion of the time that there is detection above the threshold. Thus, for a particular threshold level, if the total time for which a signal is at or above the threshold is 700 ms within a 1 s window, then the low-pulse occupancy time is 70%. The low pulse occupancy measure enables a simple binary coding of the sensor output over time; for example a binary zero output if the detected signal is above the threshold, and a binary 1 if the detected signal is below the threshold. The summed time durations of the digital zero periods correspond to the low pulse occupancy time. The combined time of the digital zero periods (per fixed unit of time) is then proportional to the analogue output signal.

In this type of sensor, the amplitude of the analog signal is proportional to the particle size, whether using particle counting or low pulse occupancy measurement. The threshold is implemented as a threshold voltage applied to a comparator which controls the particle size sensitivity of the sensor system.

Larger particles scatters a larger amount light, hence generate a larger signal amplitude at the photodetector. This analog signal (after appropriate filtering and amplification stages) is provided to the comparator.

The threshold voltage provided to the comparator sets the boundary limit for this analog signal. For example, a 1V threshold means that all signals above 1V will be registered as a detection signal, hence corresponding to all particle sizes that generate an analog signal above 1V. Likewise, a 2V threshold raises the boundary for allowing only larger sized particles to generate an output.

For simplicity a 1V threshold voltage may correspond to signals generated for particles of 1 μm diameter and above, whereas as 2V threshold may correspond to particles of 2 μm diameter and above. In order to generate particle count information for a specific particle size range (also known as a 'size bin'), for a particle size range between 1 μm and 2 μm, the number of signals generated at these threshold voltages are subtracted.

More than two threshold voltages may be used for converting the analog signal to a digitized binary output.

The sensor described above basically comprises:

a housing having an inlet and an outlet with a gas flow between them;

a light source and an optical detector for making optical scattering measurements within a detection volume, wherein the detector signal is correlated with (and for example proportional to) particle size; and a signal processor comparing the detector signal with an adjustable threshold.

The implementation of the comparison part of the signal processing may be implemented simply with a comparator with an adjustable reference voltage input.

In its simplest implementation, the invention involves measuring the detector signal at a low threshold voltage (the first threshold setting) so that as many particle sizes as possible are detected. The detector signal is also measured using a larger threshold voltage (the second threshold setting), so that only the larger particles are measured. By comparing these signals (e.g. determining the ratio of the two signals) a measure for the contribution of larger particles to the total particle mass is obtained. This provides information on the shape of the particle size distribution, and therefore on the type of event.

This knowledge of the type of event can then be used to estimate the conversion of the first signal to a value of PM2.5 (or other PM value, such as PM5 or PM10). This conversion then implements an estimation of the particle size distribution below the lower limit of sensitivity of the sensor, but without requiring measurement at those low particle sizes.

The inventors have determined that particle size distributions can differ markedly between outdoor and indoor conditions. Furthermore, for indoor conditions, the particle size distribution is largely dependent on the type of event taking place in the room.

Some results demonstrating this are given below. The results were obtained by measuring particle distributions using a professional detection system as a reference which is able to provide accurate absolute PM2.5 values.

The low cost optical sensor of FIG. 1 is however primarily sensitive for a more limited range of particle sizes (typically between about 700 and 3000 nm), which range also depends on the threshold voltage setting as explained above. For example, for cigarette smoke much of the PM2.5 mass consists of particles with a size below 700 nm.

Therefore, a ratio between the actual PM2.5 value and the signals from the sensor of FIG. 1 are dependent on the type of event.

FIGS. 2a-2d show the result of monitoring various types of indoor event in a home. Measurements were done with various sensors of the type shown in FIG. 1 and with a professional reference detector.

In FIGS. 2a-2d, the PM1, PM2.5 and PM10 results are given for dinner events on four different days.

The x-axis plots the time, and the y-axis plots the particle density in μg/m³. The vertical lines show the times between which the main pollution (e.g. dinner cooking) was taking place. The average values within these event windows are used for further analysis.

Figure 3B:
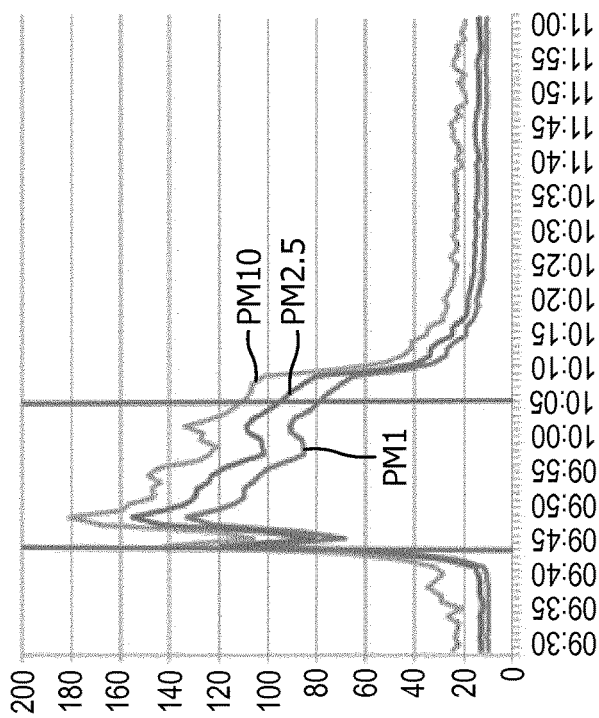
FIGS. 3a-3b show similar results to FIGS. 2a-2d for breakfast events.
Figure 3A:
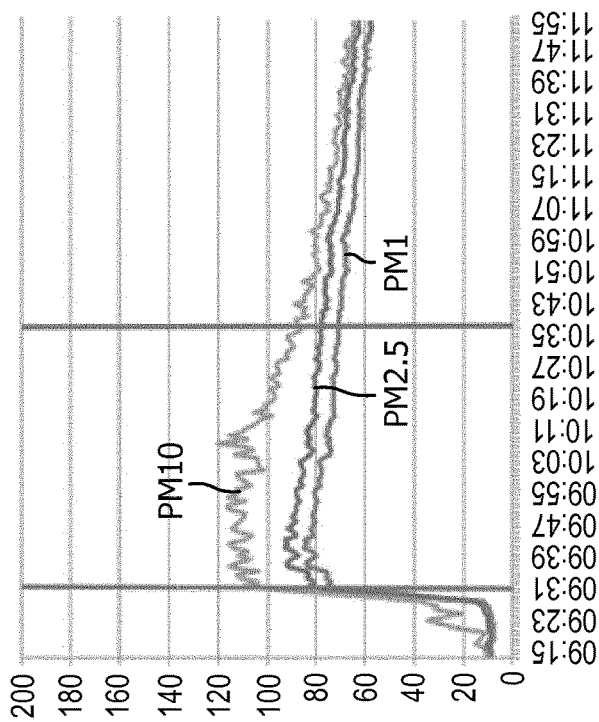

In FIGS. 3a-3b, similar results are given for two breakfast events.

Figure 4:
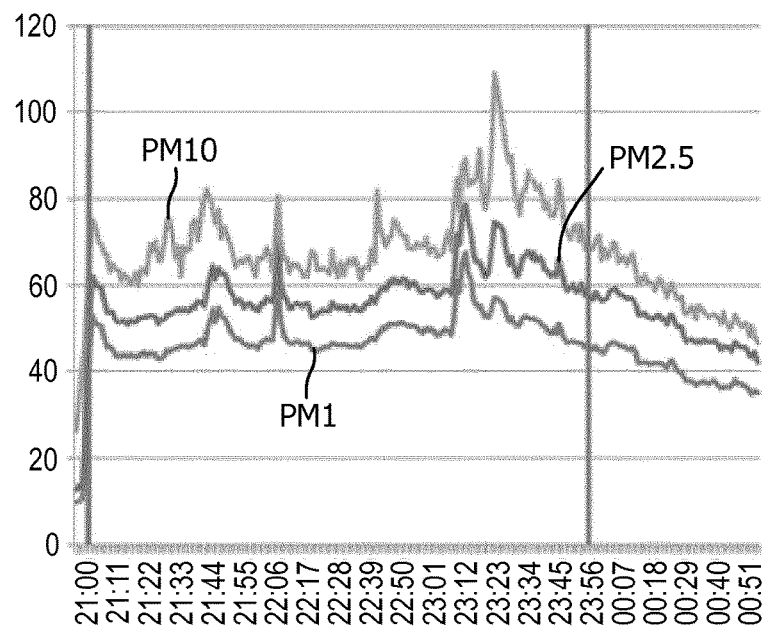
FIG. 4 shows similar results to FIGS. 2a-2d for an evening event.
Figure 5:
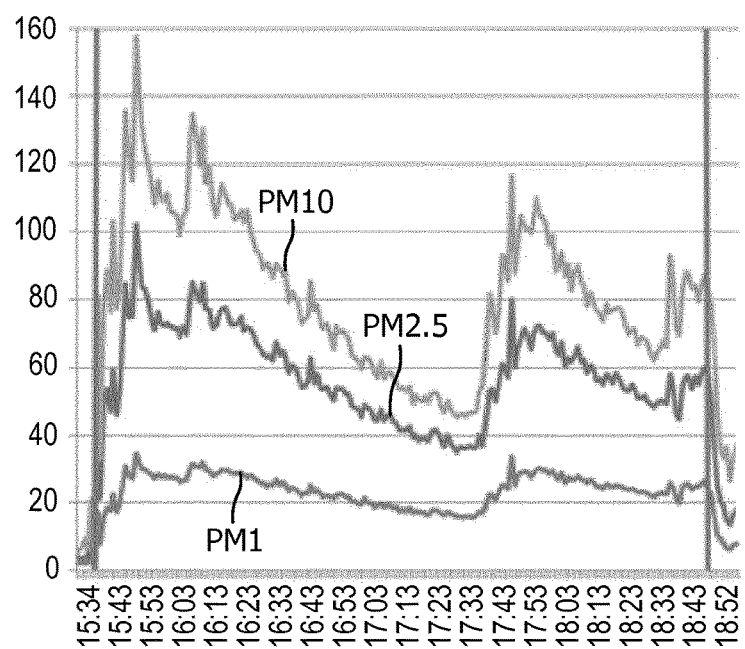
FIG. 5 shows similar results to FIGS. 2a-2d for a candle extinguishing event.

Finally, an evening event is shown in FIG. 4 which involves monitoring a full evening, and a candle extinguishing event is shown in FIG. 5.

For the dinner events of FIGS. 2a-2d, the PM10 values are much larger than the PM1 values, indicating that there is a considerable contribution of large size particle present in the air during this type of event. For the breakfast events of FIGS. 3a-3b, the PM1, PM2.5 and PM10 values are much closer together, indicating that the contribution of small particles is dominant during these events. This was also the case for the monitoring of the full 9.00 pm to midnight evening in FIG. 4.

For the candle event in FIG. 5, there is a relatively large contribution of particles of a few μm size.

The event windows as indicated above are used to take average values of the professional detector readings and also the low cost optical sensor readings.

Various possible relationships between the professional mass concentration readings and the low cost sensor readings can be analyzed. FIGS. 6a-6c and 7-9 show various plots to show the relationship between different parameters. In each case, the symbol 60 is for the dinner event, the symbol 62 is for the candle event, the symbol 64 is for the long evening event and the symbol 66 is for the breakfast event.

Figures 6A, 6B, 6C:
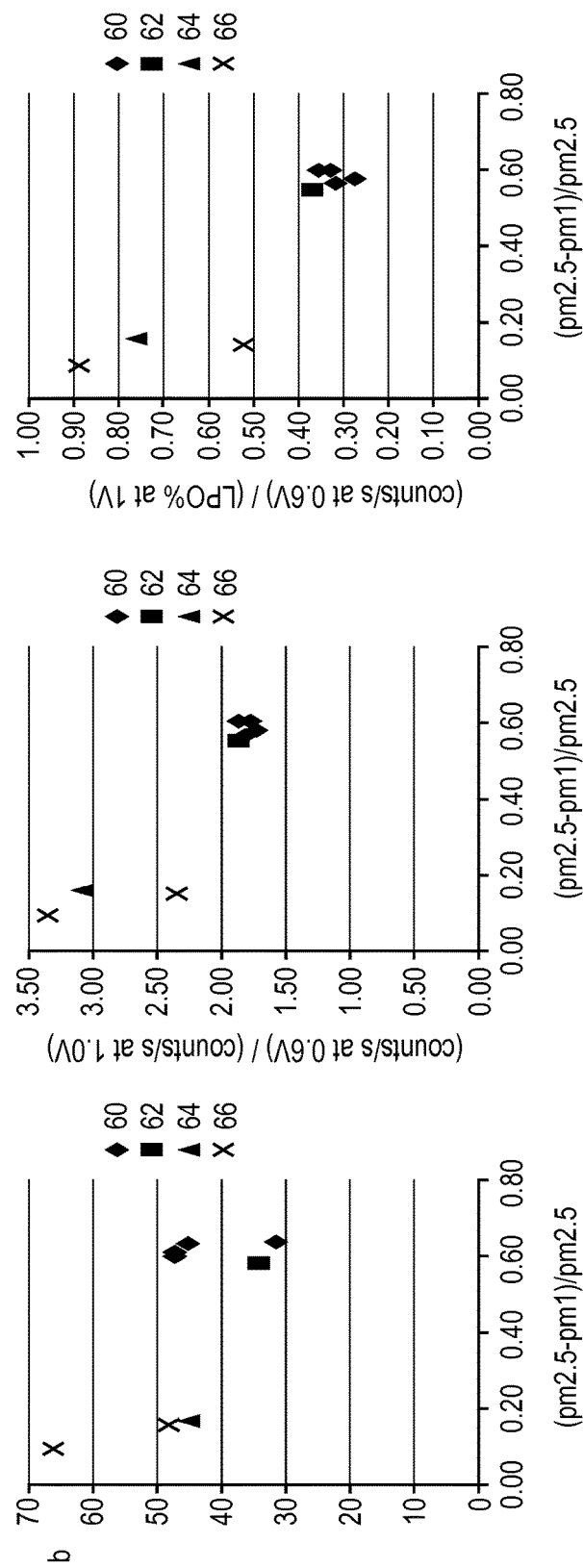
FIGS. 6a-6c show various possible relationships between the professional mass concentration readings and low cost sensor readings.

FIG. 6a shows the different events on a plot in which:
the y axis is a calibration factor b (which is the ratio of professional PM2.5 mass measurement in μg/m³ and counts/s reading of the low cost sensor) at a first (e.g. 0.6 V) threshold setting;
the x-axis is the fraction of the PM2.5 mass of particles between 1 μm and 2.5 μm size, as measured by the professional reference instrument.

The significance of the calibration parameter b is that, if it can be determined, it provides a conversion from the low cost sensor reading (at the first threshold) to the desired actual PM2.5 value.

FIG. 6b shows the different events on a plot in which:
the y-axis shows the ratio between the counts at the first threshold (0.6 V) and the second threshold (1.0 V) for the low cost sensor;
the x-axis is the fraction of the PM2.5 mass of particles between 1 μm and 2.5 μm size, as measured by the professional reference instrument.

FIG. 6c shows the different events on a plot in which:
the y-axis shows the ratio between the counts at the first threshold (0.6 V) and the LPO % at the second threshold (1.0 V).
the x-axis is the fraction of the PM2.5 mass of particles between 1 μm and 2.5 μm size, as measured by the professional reference instrument.

FIG. 6a shows that particularly the breakfast events which have a large contribution of small particles show larger b values compared with the dinner events. This can be understood from the relatively low presence of particle sizes between 1 and 2.5 μm for which the low cost sensor is sensitive, leading to a reduced sensitivity and therefore larger value of b.

This effect is even stronger if the results at 1.0V threshold setting are used, as in FIG. 6b. The ratio of measured counts/s at 0.6 V and counts/s at 1.0 V is plotted as a function of the relative mass of particles between 1.0 and 2.5 μm. This ratio is very different between the dinner and the breakfast events. This is consistent with the fact that at 1.0V the low cost sensor excludes more of the small particles than at 0.6V.

In FIG. 6c the ratio of the counts/s at 0.6 V and the LPO % value at 1.0 V is used to form a parameter. The difference between the dinner and breakfast events is even still stronger than for the counts at 1.0 V.

These results suggest that the ratio of the measured counts/s (0.6 V) to the LPO % (1.0 V) may be used as a parameter of interest, and thus a fingerprint for the type of event. The mapping works for events with dominantly small particles, or events with dominantly large particles.

Figure 7:
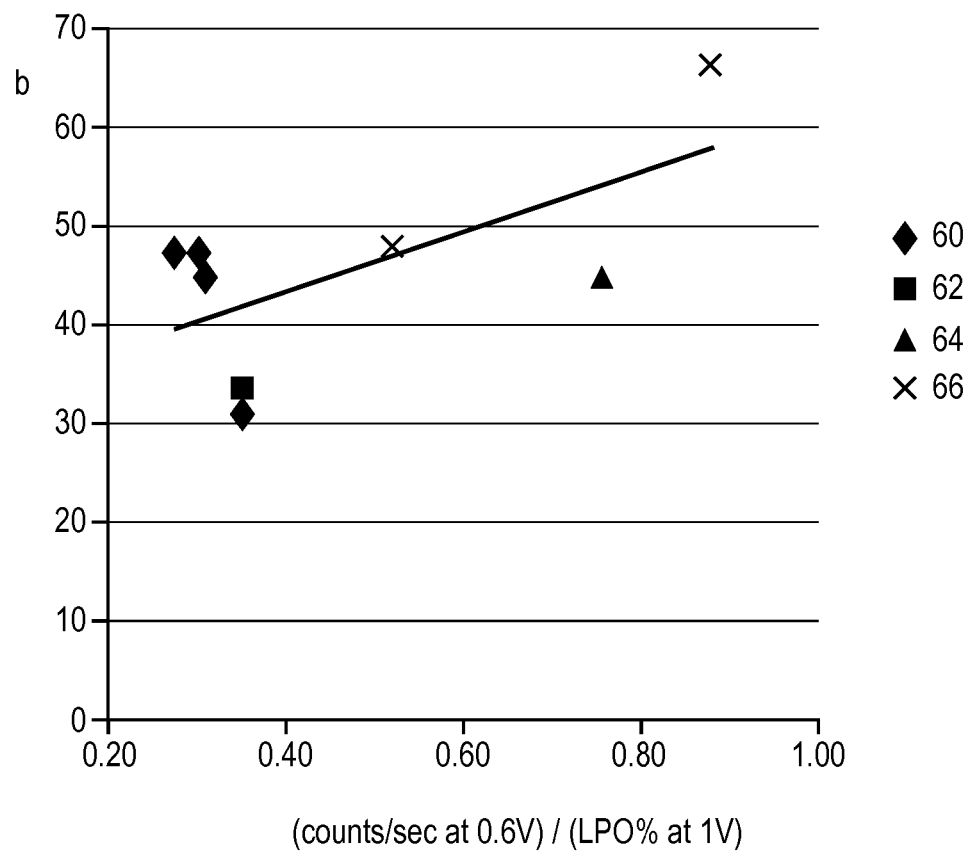
FIG. 7 shows different events on a plot of a calibration factor versus a ratio between the counts at a first threshold and the LPO % at a second threshold.

FIG. 7 shows the different events on a plot in which:
the y axis is the calibration factor b (which is the ratio of professional PM2.5 mass measurement in μg/m³ and counts/s reading of the low cost sensor) at a first (e.g. 0.6 V) threshold setting;
the x-axis shows the ratio between the counts at the first threshold (0.6V) and the LPO % at the second threshold (1.0 V).

FIG. 7 shows that there is a function (e.g. the best fit line shown in FIG. 7) which maps between the two combined low cost sensor readings (at the two thresholds) and the desired calibration value b.

Using the example of FIG. 7, the ratio between the counts at the first threshold (0.6 V) and the LPO % at the second threshold (1.0 V) may be defined as a "parameter". This parameter is dependent on the type of pollution event, since as shown, different events give rise to different values along the x-axis. The parameter can then be used to determine a mass of all particles below a first particle size. This is carried out by converting the parameter to the calibration value b (using the best fit line in FIG. 7), and the calibration value b then maps the low cost sensor reading at the lower threshold to the desired PM value. Thus, the calibration value b can be used to modify the first optical sensor reading to derive the sensed mass of all particles below the first particle size (e.g. 2.5 μm).

In this example, the particle count per unit time for the first threshold setting is combined with a low pulse occupancy rate for the second threshold setting.

However, other parameters are also possible which can be mapped to the calibration value b, such as by combining a particle count per unit time for the first threshold setting and a particle count per unit time for the second threshold setting. This also provides a possible mapping as can be seen from FIG. 6b.

The knowledge of the type of event (as embodied by the selected parameter) is then used to derive the absolute value of b for converting the counts/s data at the first threshold setting into total mass concentration data.

The invention can essentially be implemented by operating suitable software either at the controller 24 of the sensor device, or partly at the sensor device (e.g. to control the application of different thresholds) and partly remotely (e.g. processing the sensor data) or else entirely remotely if the thresholds can be applied only as data processing of raw data.

The approach of the invention has been tested by deriving a transfer function model for the professional detector and for the low cost optical sensor, and then processing different theoretical particle mass distributions.

Figure 8:
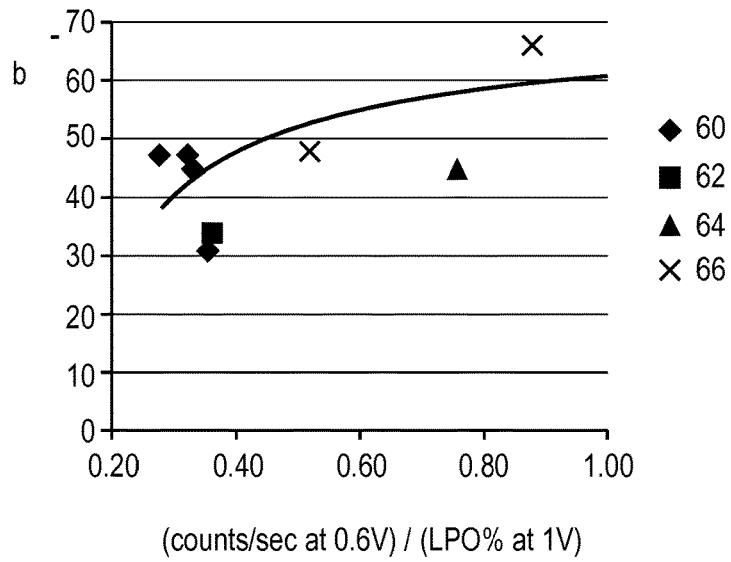
FIG. 8 shows the same experimental results as FIG. 7 with a function line which is the result of the modeling of the transfer functions of the low cost sensor and the professional sensor.

FIG. 8 shows the same experimental results as FIG. 7. It also shows a line which is the result of the modeling of the transfer functions of the low cost sensor and the professional sensor. Thus, the function used to map from the measured parameter (in this case the ratio of counts/s at the first threshold to the LPO % at the second threshold) to the calibration value b may not be a best fit line, but may be a non-linear function.

In conclusion, in one example, the type of pollution can be found from a parameter which is the measured ratio of count/s at 0.6 V and LPO % at 1.0 V. Using the relationship of FIG. 8, the corresponding calibration factor b for this event can then be determined.

Alternatively, a parameter which is a measured ratio of counts/s at 0.6V and counts/s at 1.0 V can also be used to derive the type of event.

Figure 9:
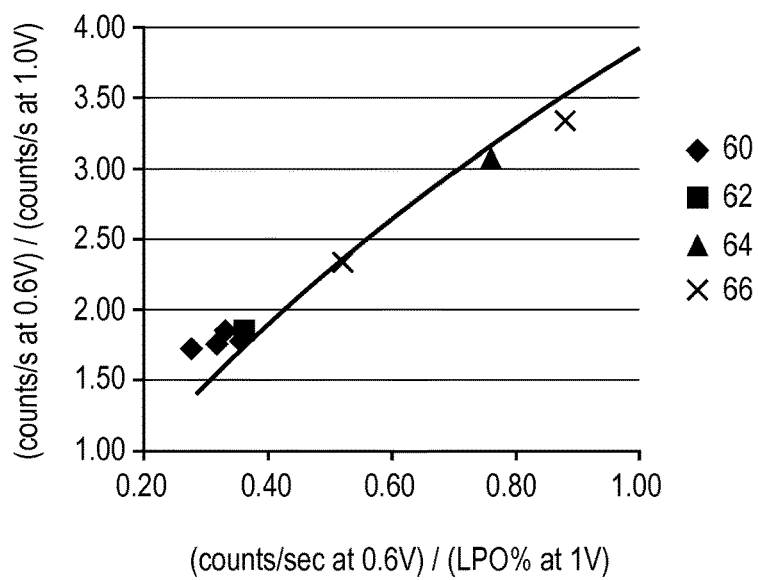
FIG. 9 shows a relationship between the ratio of counts/s at first and second thresholds and the ratio of counts/s at a first threshold and LPO % at a second threshold.

As shown in FIG. 9, based on the same transfer function modeling as used in FIG. 8, there is a relationship between (i) the ratio of counts/s at the first and second thresholds and (ii) the ratio of counts/s at the first threshold and LPO % at the second threshold. The solid line is the relationship derived from modeling (it is not a straight line) and the experimental results show a good fit.

Thus, based on only counts/s measurements, a corresponding ratio for counts/s at 0.6 V and LPO % at 1.0 V can be derived using the relationship of FIG. 9. Then, FIG. 8 can be used to determine the corresponding calibration factor b for this event.

Of course, in practice all calculations are in software so there is no need to map from the relationship of FIG. 9 to FIG. 8. There can instead be a direct function between the counts/s ratio and the calibration value b.

It is also possible to use counts/s or LPO % values measured at threshold voltages at third or further thresholds (e.g. larger than 1.0 V). Additional measurements may give an even more sensitive measure for the type of event, however these measurements may be more affected by the influence of noise (e.g. shot noise due to the lower particle number counts at these larger threshold voltages).

The measurement at two or more different threshold settings may be simultaneous at two or more different detection ports of the sensor, or at sequential times at the same port.

The threshold may also be applied in software after a capture of all relevant sensor information, for example a sensor signal based on a sweep of threshold values.

The invention is of interest for particle concentration detectors such as forming part of air purifier systems for indoors, by optical light scattering. However, as well as measurements of particles in air (or other gases), similar approaches can be adopted for particle sensors in fluids.

Another aspect of this invention relates to the selection of information to be displayed to the user of the sensor device. Advanced user interfaces for communicating the readings of these sensors can be an integral part of an appliance or else the appliance may send data to a remote device for display such as a mobile phone or tablet, via a designated application.

A number of application designs are available for various platforms for communicating with sensors, and displaying the sensor readings to the user, and also displaying other relevant data from other sources. An example of such an application that contains local information and other relevant information is the user interface of a Philips® Air Purifier. The application shows the local air quality index measured by the sensors on the appliance, as well as the outdoor air quality index acquired from publicly available sources. This is a typical example of a data rich user interface.

A particle sensor typically requires a stabilization time during start-up or during the periods when the concentration changes dramatically. During this period sensor readings are not as steady as they are in stable conditions.

Figure 10:
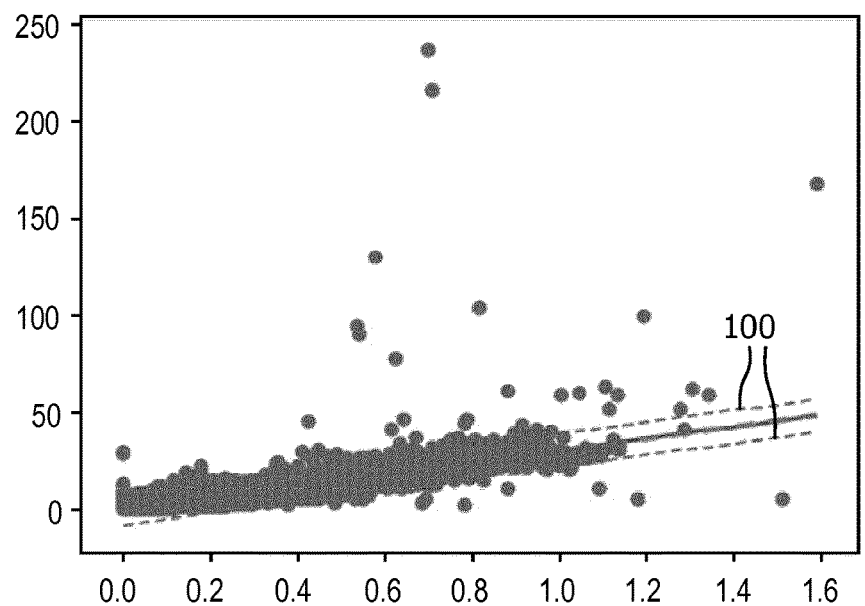
FIG. 10 shows a first regression analysis of the sensor data compared to a reference instrument for data averaged over 1 minute.
Figure 11:
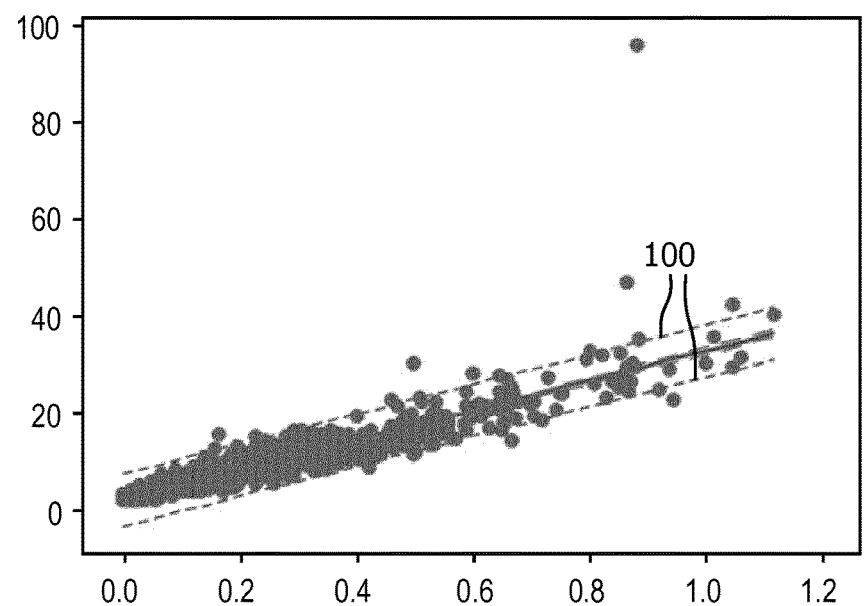
FIG. 11 shows a second regression analysis of the sensor data compared to a reference instrument for data averaged over 10 minutes.
Figure 12:
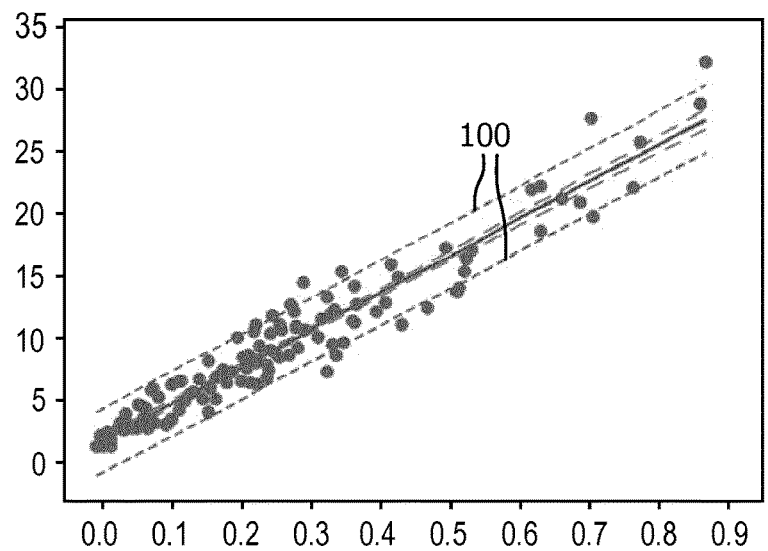
FIG. 12 shows a third regression analysis of the sensor data compared to a reference instrument for data averaged over 1 hour.

An example of this problem is shown in FIGS. 10 to 12, which show the accuracy of the same sensor unit, for predicting the actual concentration in the same environment for 1 minute, 10 minute and 1 hour sampling times, respectively.

Each of FIGS. 10 to 12 shows a regression analysis of the sensor data compared to a reference instrument. Each plot is of actual concentration versus sensor signal (in arbitrary units). The dashed lines 100 show the 90% prediction interval. The success rate of the linear relationship between the sensor and the reference instrument is 59.9% for the 1 minute data, 79.1% for the 10 minute data and 93.6% for the 1 hour data.

As can be seen from FIGS. 10 to 12, the success rate of the sensor increases dramatically for longer averaging times. The same applies to different types of sensors, which may benefit from longer integration times, as well as longer data averaging periods.

Figure 13:
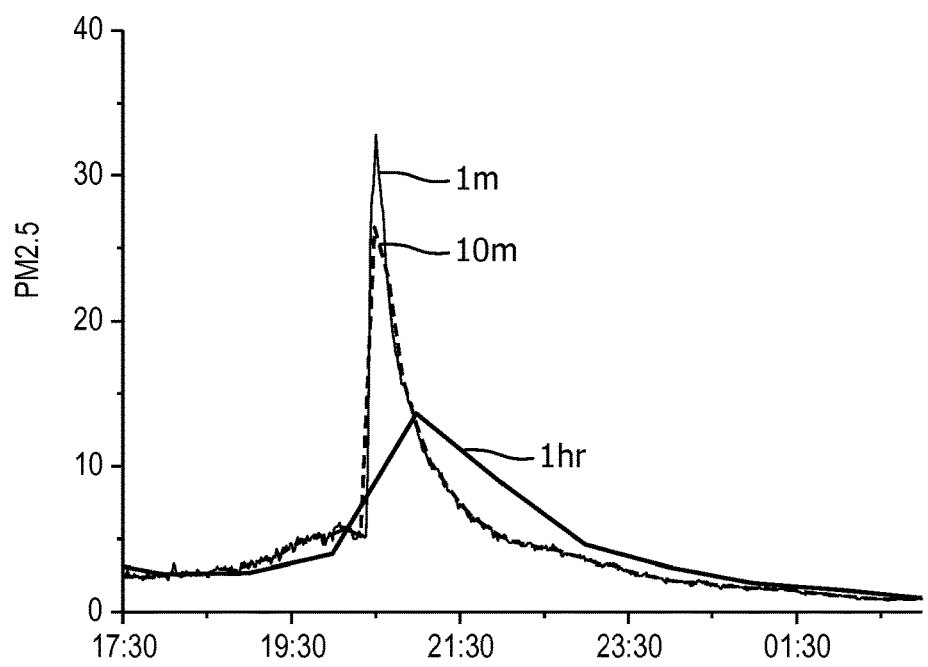
FIG. 13 is a first graph to show the effect of applying moving data averaging on the represented sensor value, for PM2.5 measurements.
Figure 14:
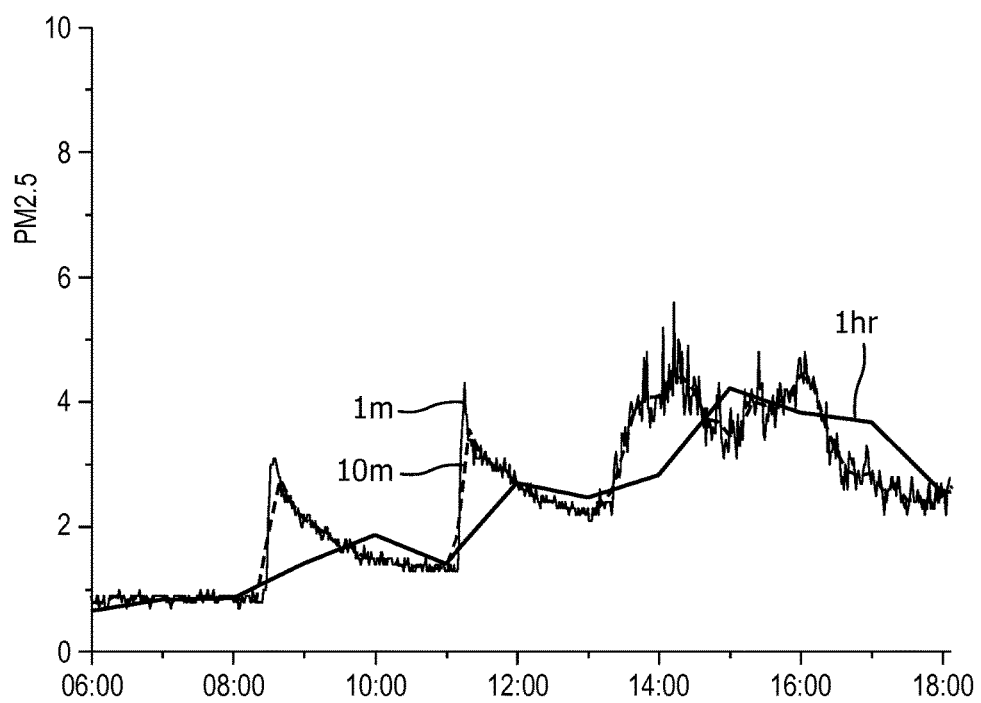
FIG. 14 is a second graph to show the effect of applying moving data averaging on the represented sensor value, for PM2.5 measurements.

FIGS. 13 and 14 shows the effect of applying moving data averaging on the represented sensor value, for PM2.5 measurements. Three plots are shown, for averaging windows of 1 minute, 10 minutes and 1 hour. The y-axis shows the PM2.5 value as displayed and the x-axis shows the time.

In FIG. 13, there is a large detection event at 20:30. The longer the averaging time window, the longer it takes to reach the peak value and the peak value is suppressed.

In FIG. 14, there is a sequence of smaller detection events. The minor peaks will be lost in the sensor readings as a result of long term (e.g. hourly) moving averaging of the sensor data.

If the data is represented with long averaging time (i.e. integrating time or sampling time) the data is more accurate for static conditions. However, this will result in misleading communication to users during sudden concentration changes when there is a stimulus for sensor response, as the displayed data shows the effect of the event only at the end of the averaging time, which may be already long after the event has occurred. For example, in the case of a particle sensor, using hourly averaging has the benefit of providing data at higher reliability, as demonstrated in FIGS. 10 to 12 but the visibility and the level of short term events that generate a peak in concentration will be significantly affected by the long term data averaging, as shown in FIGS. 13 and 14. The averaging can also lead to complete loss of some minor peaks in the sensor readings, as shown in FIG. 14.

These mismatches have a negative influence on the user perception and sometimes can be even misleading for consumers as they may perceive them as an error in the sensor readings.

The sensor typically implements storage, averaging, and filtering of the mass data obtained. The processed data is either displayed by the sensor device or it may be sent to a remote user interface and/or to an external data storage facility, by a wired or wireless link.

When the sensor information is displayed to a user (either at the sensor or remotely), the data averaging behavior is, in accordance with this additional feature of the invention, controlled to optimize the user experience.

In particular, a first mass signal and a second moving average mass signal are prepared, and an output is provided for display which comprises one of the first and second mass signals. The first mass signal may be the most immediate output that the sensor can provide—but this may still involve integration over a time period, for example 10 s. Thus, it may be as real time as the sensor is able to produce.

The first mass signal is stored at least for the duration of the longest averaging time to be employed. The memory also stores the required data processing, filtering and averaging algorithms/codes, etc.

Figure 15:
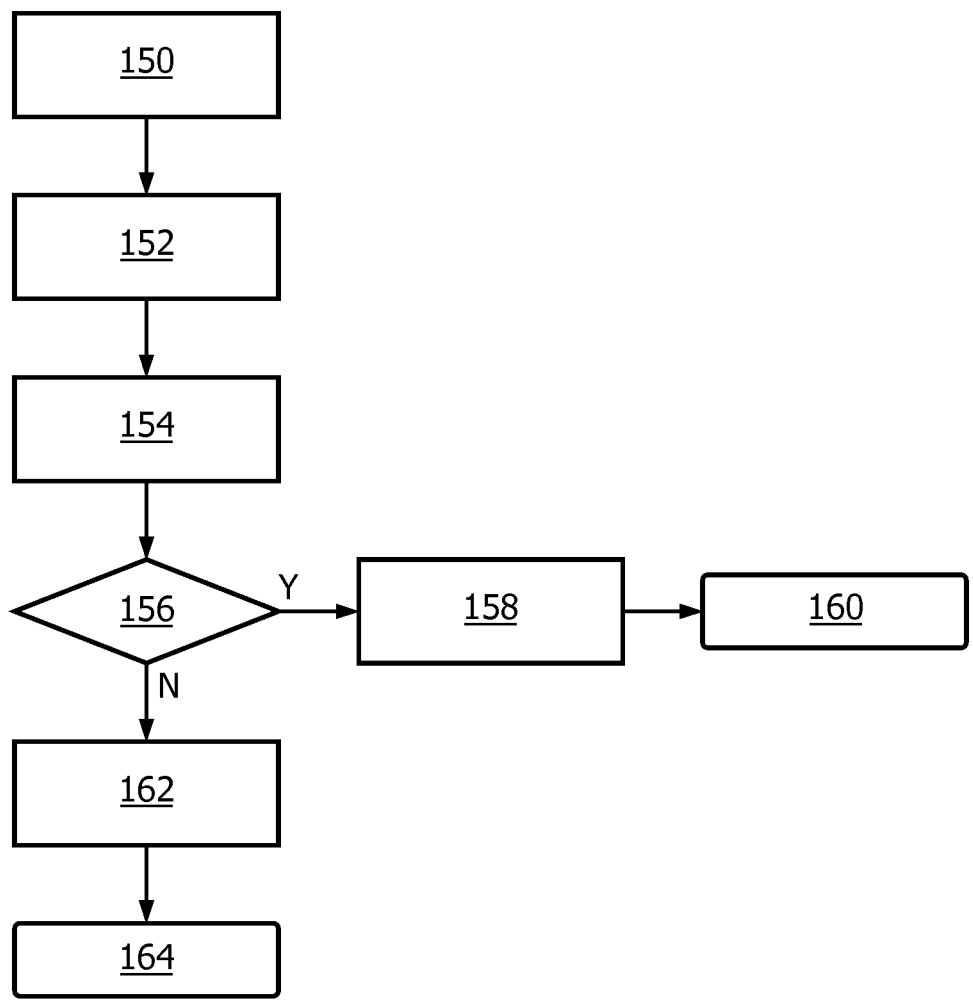
FIG. 15 shows a method of selecting the data to be displayed.

FIG. 15 shows a method of selecting the data to be displayed, based on a simplified approach of having only two choices of data.

The real time data is obtained in step 150 and is stored in step 152.

One or more moving point averages are taken in step 154. Only one moving point average is needed if the raw data is the other data choice. If two averages are taken, they have different averaging windows and they then provide the two data choices.

In step 156 it is determined if the moving average with a shorter averaging window (i.e. the real time data or the moving average data with the shorter window) is significantly different to the data with the longer averaging time. If the shorter averaged data is different, this means there are local peaks which have been averaged out in the longer averaged data. Then, the shorter averaged data is displayed in step 158 and the process ends in step 160. If the data is close, the longer averaged data is displayed in step 162 and the process ends in step 164. In this way, the peak detection quality is linked to the display function. If the level of the real time data significantly differs from the averaged value, then it indicates the presence of a positive or a negative peak in the measured variable.

This process can be extended to more than two data choices.

Figure 16:
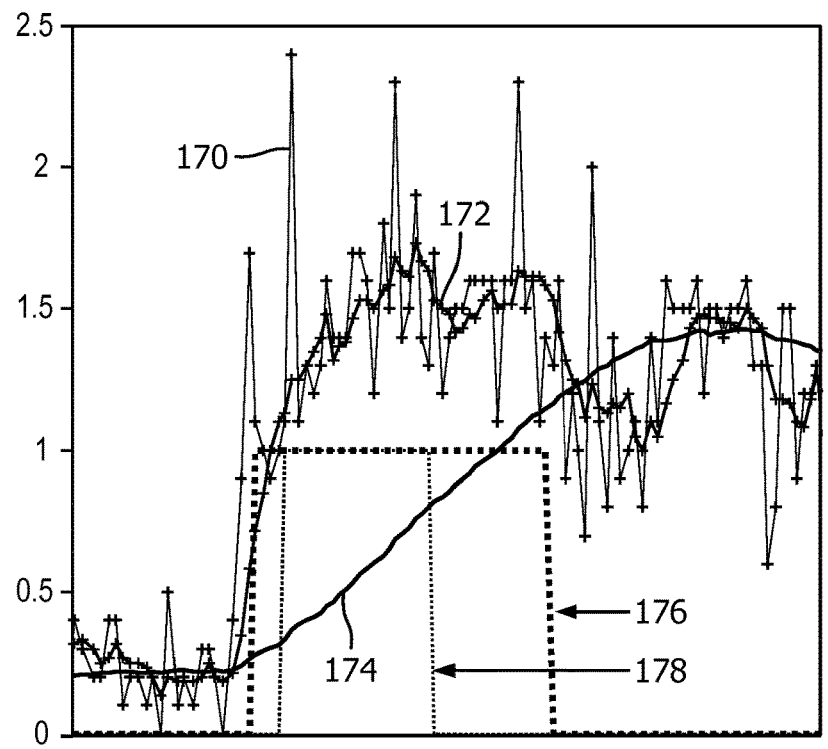
FIG. 16 shows three different output data streams, each in counts/s.

FIG. 16 shows three different output data streams, each in counts/s. The raw data is plot 170 (but this has an averaging time of e.g. 10 s), plot 172 is data averaged over a short window (n=6 samples, i.e. 1 minute) and plot 174 is data averaged over a longer window (n=60 samples, i.e. 10 minutes).

The plot 176 is a comparison result. It is 1 if the difference between the two moving averages exceeds a threshold of 0.4 counts/s and is 0 if the difference of the moving averages less than threshold of 0.4 counts/s.

Because the two signals being compared are both averaged (over different times), there should not be spikes in the comparison result. Even if there are some short duration changes in display mode, these will not be unpleasant for the user if there is continuity between the display modes.

The plot 178 is a comparison result with a higher threshold of 0.8 counts/s.

The comparison result then controls the information to be displayed. During the time when the comparison is 1, the plot 172 (or even 170) is presented to the user, whereas during the time when the comparison is 0, plot 174 is presented to the user.

Generally, the display distinguishes between steady data, when more accurate longer averaged data is displayed, and moving data, when less accurate but more responsive data is displayed.

There are other display options. For example, when there is moving data, a blinking or fading or different color output can be used to provide a warning that a detection event is taking place. The moving data and steady data may both be represented on the display at the same time to provide additional information.

Figure 17:
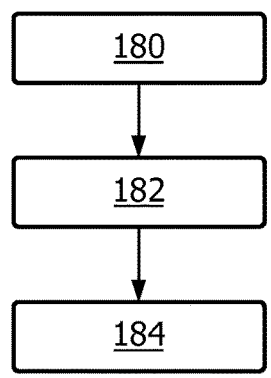
FIG. 17 is a flow chart for showing the general particle sensing method of the invention.

FIG. 17 is a flow chart for showing the general particle sensing method of the invention.

In step 180, an optical sensor is operated to generate a sensor signal.

First and second threshold settings are applied either during sensing or during subsequent data processing, in order to obtain first and second sensor readings. As explained above, the threshold setting dictates a particle size detection range captured by the sensor signal.

In step 182 the first and second optical sensor readings are processed to determine therefrom a parameter which depends on the type of pollution event.

In step 184 the parameter is used to determining from at least one of the first and second optical sensor readings a mass of all particles below a first particle size. As discussed above, embodiments make use of a controller to implement the processing of the sensor information. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs). In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions.

Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An optical particle sensor, comprising:
an optical sensor which generates a sensor signal, wherein the sensor signal or an analysis of the sensor signal is controllable by applying a threshold setting, wherein the threshold setting dictates a particle size detection range captured by the sensor signal; and
a controller adapted to:
apply at least first and second different threshold settings and receive corresponding first and second optical sensor readings;
process the first and second optical sensor readings to determine therefrom a parameter which is dependent on a type of pollution event and thereby identify the pollution event; and
use a particle size profile which relates to the identified pollution event to determine from at least one of the first and second optical sensor readings a mass of all particles below a first particle size.

2. The sensor as claimed in claim 1, wherein the optical sensor is only sensitive to particles above a second particle size, below the first particle size.

3. The sensor as claimed in claim 1, wherein the first threshold setting is for detecting a wider range of particle sizes than the second threshold setting.

4. The sensor as claimed in claim 1, wherein the controller is adapted to modify one of the first and second optical sensor readings based on the parameter to derive the sensed mass of all particles below the first particle size.

5. The sensor as claimed in claim 1, wherein the optical sensor provides at least one of a measure of counts per unit time and a measure of low pulse occupancy percentage after digitization of an analog signal by a comparator, wherein for providing a measure of low pulse occupancy percentage, the optical sensor comprises a light source and a light detector for measuring scattered signal pulses and the controller is adapted to provide a count of scattered signal pulses exceeding a height threshold and to determine a proportion of time during which there is detection above the height threshold.

6. The sensor as claimed in claim 1, comprising a display for displaying information conveying the mass of all particles below the first particle size, wherein the controller is adapted to generate a first mass signal and a second, moving average, mass signal, wherein the first mass signal is a real time sensor signal or a moving average signal averaged over a shorter duration than the second mass signal, and the processor is adapted to provide an output for display comprising one of the first and second mass signals.

7. The sensor as claimed in claim 5, wherein the controller is adapted to process the first and second optical sensor readings by: combining a particle count per unit time for the first threshold setting and a low pulse occupancy rate for the second threshold setting; or combining a particle count per unit time for the first threshold setting and a particle count per unit time for the second threshold setting.

8. The sensor as claimed in claim 6, wherein the controller is adapted to select one of the first and second mass signals in dependence on a difference between them.

9. An optical particle sensing method, comprising:
operating an optical sensor to generate a sensor signal, controlling the sensor or analyzing the generated sensor signal by applying at least first and second different threshold settings to obtain first and second sensor readings, wherein the different threshold settings dictate a corresponding particle size detection range captured by the sensor signal;
processing the first and second optical sensor readings to determine therefrom a parameter which depends on a type of pollution event and thereby identify the type of pollution event; and
using a particle size profile which relates to the identified pollution event to determine from at least one of the first and second optical sensor readings a mass of all particles below a first particle size.

10. A The method as claimed in claim 9, comprising:
processing the first and second optical sensor readings by combining a particle count per unit time for the first threshold setting and a low pulse occupancy rate for the second threshold setting; or
processing the first and second optical sensor readings by combining a particle count per unit time for the first threshold setting and a particle count per unit time for the second threshold setting.

11. The method as claimed in claim 9, wherein the first threshold setting is for detecting a wider range of particle sizes than the second threshold setting.

12. The method as claimed in claim 9, comprising modifying one of the first and second optical sensor readings based on the parameter and thereby deriving the mass of all particles below the first particle size.

13. The method as claimed in claim 9, comprising displaying information conveying the mass of all particles below the first particle size, wherein the method further comprises generating a first mass signal and a second, moving average, mass signal, wherein the first mass signal is a real time sensor signal or a moving average signal averaged over a shorter duration than the second mass signal, and displaying one of the real time mass signal and the moving average signal.

14. The method as claimed in claim 9, wherein the first and second optical sensor readings are taken sequentially at a same sensor location or simultaneously at different sensor locations.

15. A nontransitory medium encoded with a computer program comprising computer code which is adapted, when run on a computer, to implement an optical particle sensing method, comprising:
operating an optical sensor to generate a sensor signal, controlling the sensor or analyzing the generated sensor signal by applying at least first and second different threshold settings to obtain first and second sensor readings, wherein the different threshold settings dictate a corresponding particle size detection range captured by the sensor signal;
processing the first and second optical sensor readings to determine therefrom a parameter which depends on a type of pollution event and thereby identify the type of pollution event; and using a particle size profile which relates to the identified pollution event to determine from at least one of the first and second optical sensor readings a mass of all particles below a first particle size.

* * * * *